US011583560B2

(12) United States Patent
Cho et al.

(10) Patent No.: US 11,583,560 B2
(45) Date of Patent: Feb. 21, 2023

(54) IMMUNOMODULATORY COMPOSITION COMPRISING LACTOBACILLUS-DERIVED EXTRACELLULAR VESICLES

(71) Applicant: AMOREPACIFIC CORPORATION, Seoul (KR)

(72) Inventors: Eun-Gyung Cho, Yongin-si (KR); Wanil Kim, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 262 days.

(21) Appl. No.: 16/759,892

(22) PCT Filed: Oct. 5, 2018

(86) PCT No.: PCT/KR2018/011787
§ 371 (c)(1),
(2) Date: Apr. 28, 2020

(87) PCT Pub. No.: WO2019/088478
PCT Pub. Date: May 9, 2019

(65) Prior Publication Data
US 2021/0177919 A1 Jun. 17, 2021

(30) Foreign Application Priority Data
Oct. 31, 2017 (KR) .................. 10-2017-0143640

(51) Int. Cl.
*A61K 35/747* (2015.01)
*A23L 33/135* (2016.01)
(Continued)

(52) U.S. Cl.
CPC .......... *A61K 35/747* (2013.01); *A23L 33/135* (2016.08); *A61K 8/14* (2013.01); *A61K 8/99* (2013.01)

(58) Field of Classification Search
CPC .................................................. A61K 35/747
See application file for complete search history.

(56) References Cited

U.S. PATENT DOCUMENTS

| 2015/0246084 A1 | 9/2015 | Park et al. |
| 2015/0250834 A1 | 9/2015 | Tsai et al. |
| 2018/0055894 A1 | 3/2018 | Kim et al. |

FOREIGN PATENT DOCUMENTS

| JP | 2007-070249 A | 3/2007 |
| JP | 2014-031325 A | 2/2014 |

(Continued)

OTHER PUBLICATIONS

Jang et al., "*Lactobacillus plantarum* CLP-0611 ameliorates colitis in mice by polarizing M1 to M2-like macrophages", International Immunopharmacology, 2014, vol. 21, pp. 186-192 (7 pages total).

(Continued)

*Primary Examiner* — Benjamin J Packard
(74) *Attorney, Agent, or Firm* — Sughrue Mion, PLLC (57) ABSTRACT

The present specification discloses an immunomodulatory composition comprising lactobacillus-derived extracellular vesicles as an active ingredient. The lactobacillus may be *Lactobacillus plantarum*. The composition has the effects of inducing differentiation into M2-type macrophages and reducing expression of at least one member selected from the group consisting of CCR2, SOCS3 and HLA-DRα, which are M1-type macrophage differentiation markers.

7 Claims, 8 Drawing Sheets

(51) Int. Cl.
    *A61K 8/14*    (2006.01)
    *A61K 8/99*    (2017.01)

(56) References Cited

FOREIGN PATENT DOCUMENTS

| KR | 10-0742900 B1    | 7/2007  |
|----|------------------|---------|
| KR | 10-2013-0000003 A | 1/2013  |
| KR | 10-2014-0055397 A | 5/2014  |
| KR | 10-1629525 B1    | 6/2016  |
| KR | 10-2016-0110232 A1 | 9/2016 |
| KR | 10-2017-0109822 A | 10/2017 |
| WO | 2010/027344 A1   | 3/2010  |
| WO | 2016/057755 A1   | 4/2016  |
| WO | 2016/144139 A2   | 9/2016  |

OTHER PUBLICATIONS

Korean Intellectual Property Office, Office Action dated Jun. 24, 2021 in Korean Application No. 10-2017-0143640.
Ming Li et al., "Lactobacillus-derived extracellular vesicles enhanced host immune responses against vancomycin-restraint enterococci", BMC Microbiology, Mar. 14, 2017, pp. 1-8, vol. 17, Document No. 66.
Jeroen Van Bergenhenegouwen et al., "Extracellular Vesicles Modulate Host-Microbe Responses by Altering TLR2 Activity and Phagocytosis", Plos One, Feb. 2014, pp. 1-11, vol. 9, No. 2, document No. e89121.
International Search Report for PCT/KR2018/011787 dated Feb. 11, 2019 [PCT/ISA/210].
Khalid Al-Nedawi et al., "Gut commensal microvesicles reproduce parent bacterial signals to host immune and enteric nervous systems", The FASEB Journal, 2014, vol. 29, No. 2, pp. 684-695 (12 pages total).
Jose Alberto Molina-Tijeras et al., "The Immunomodulatory Properties of Extracellular Vesicles Derived from Probiotics: A Novel Approach for the Management of Gastrointestinal Diseases", Nutrients, 2019, vol. 11, No. 1038, pp. 1-15 (15 pages total).
Marie-Ange Dagnelie et al., "Bacterial extracellular vesicles: A new way to decipher hostmicrobiota communications in inflammatory dermatoses", Experimental Dermatology, 2019, vol. 29, pp. 22-28 (7 pages total).
Wanil Kim et al., "Lactobacillus plantarum-derived extracellular vesicles induce anti-inflammatory M2 macrophage polarization in vitro", Journal of Extracellular Vesicles, 2020, vol. 9, No. 1793514, pp. 1-15 (15 pages total).
Extended European Search Report dated Nov. 12, 2021 in Application No. 18873459.4.

IMMUNOMODULATORY COMPOSITION COMPRISING LACTOBACILLUS-DERIVED EXTRACELLULAR VESICLES

This application is a U.S. National Stage Application under 35 U.S.C. § 371 of International Patent Application No. PCT/KR2018/011787 filed Oct. 5, 2018, which claims the benefit of priority to Korean Patent Application No. 10-2017-0143640 filed Oct. 31, 2017, the disclosures of all of which are hereby incorporated by reference in their entireties. The International Application was published in Korean language on May 9, 2019 as WO2019/088478.

TECHNICAL FIELD

The present disclosure discloses an immunomodulatory composition comprising an extracellular vesicle derived from lactic acid bacteria as an active ingredient.

BACKGROUND ART

Most animal cells have the ability to secrete extracellular vesicles of intracellular origin with varying sizes and components, and these extracellular vesicles are found in all biological fluids including blood, urine, saliva and cell culture. Prokaryotic or eukaryotic cells are also known to secrete extracellular vesicles.

Extracellular vesicles are membrane structure vesicles with diameters ranging from about 20 nm to about 5 μm. They differ in sizes and components, and include various different species, such as exosomes (about 20-100 nm), ectosomes, microvesicles (about 100-1,000 nm), microparticles, apoptotic bodies (about 1-5 μm), etc.

The different types of extracellular vesicles are distinguished based on their origin, diameter, density in sucrose, shape, precipitation speed, lipid composition, protein marker, secretion type (i.e., induced by signals (inductive) or naturally produced (constitutional)), etc. For example, the microvesicles are membrane vesicles with a size of about 100-1,000 nm and irregular shape and are known to bud toward the outside of the plasma membrane (derived from the plasma membrane) and have markers including integrin, selectin, CD40 ligand, etc. and phospholipids including phosphatidylserine. Meanwhile, the exosomes are the smallest membrane vesicles with a size of about 20-100 nm (<200 nm) and a cup shape and are known to bud from inside the late endosomes and contain, in general, markers including CD63 and CD9 tetraspanins, TSG101 and ESCRT, and lipids including cholesterol, sphingomyelin, ceramide and phosphatidylserine.

The extracellular vesicles reflect the state of the cells (donor cells) from which they are secreted, exhibit various biological activities depending on the cells from which they are secreted, and play an important role in intercellular interaction (cell-to-cell communication) as they transfer genetic materials and proteins between cells.

Lactic acid bacterium, which is the most beneficial microorganism to the human body, is a bacterium which produces organic acids such as lactic acid or acetic acid by degrading sugars such as glucose or lactose. Although the lactic acid bacterium is used to prepare fermented food such as fermented milk, cheese or butter through a fermentation process to produce organic acids from sugars, nothing is known about the immunomodulatory effect of an extracellular vesicle derived from the lactic acid bacterium.

REFERENCES OF RELATED ART

Patent Documents

Korean Patent Publication No. 10-2017-0109822.

DISCLOSURE

Technical Problem

In an aspect, the present disclosure is directed to providing an immunomodulatory composition which comprises an extracellular vesicle, which is a complex physiologically active substance derived from lactic acid bacteria as an active ingredient.

Technical Solution

In an aspect, the present disclosure provides an immunomodulatory composition comprising an extracellular vesicle derived from lactic acid bacteria as an active ingredient.

In an exemplary embodiment, the lactic acid bacteria may be a strain in the genus *Lactobacillus*.

In an exemplary embodiment, the strain in the genus *Lactobacillus* may be *Lactobacillus plantarum*.

In an exemplary embodiment, the *Lactobacillus plantarum* may be *Lactobacillus plantarum* APsulloc 331261 having an accession number of KCCM11179P.

In an exemplary embodiment, the extracellular vesicle may be an exosome.

In an exemplary embodiment, the extracellular vesicle may have a diameter of 20-200 nm.

In an exemplary embodiment, the composition may induce differentiation into M2 type macrophages.

In an exemplary embodiment, the composition may increase expression of one or more selected from a group consisting of CCL19, CCL20 and VEGFA, which are M2 type macrophage differentiation markers.

In an exemplary embodiment, the composition may decrease expression of one or more selected from a group consisting of CCR2, SOCS3 and HLA-DRα, which are M1 type macrophage differentiation markers.

In an exemplary embodiment, the composition may be a cosmetic composition.

In an exemplary embodiment, the composition may be a food composition.

Advantageous Effects

In an aspect, the present disclosure provides an effect of providing an immunomodulatory composition which comprises an extracellular vesicle, which is a complex physiologically active substance derived from lactic acid bacteria as an active ingredient.

BEST MODE

Hereinafter, the present disclosure is described in detail.

In an aspect, the present disclosure provides an immunomodulatory composition comprising an extracellular vesicle derived from lactic acid bacteria as an active ingredient.

In another aspect, the present disclosure provides an immunomodulatory method comprising applying an extracellular vesicle derived from lactic acid bacteria of an amount effective for immunomodulation to a subject in need thereof.

In another aspect, the present disclosure provides an extracellular vesicle derived from lactic acid bacteria for use in immunomodulation of a subject.

In another aspect, the present disclosure provides a non-therapeutic use of an extracellular vesicle derived from lactic acid bacteria for use in immunomodulation of a subject.

In another aspect, the present disclosure provides a use of an extracellular vesicle derived from lactic acid bacteria in manufacturing an immunomodulatory composition.

In an exemplary embodiment, the extracellular vesicle derived from lactic acid bacteria may be applied, or administered, or spreaded to a subject in the form of a composition, e.g., a cosmetic composition, a pharmaceutical composition or a food composition.

In an exemplary embodiment, the extracellular vesicle derived from lactic acid bacteria may be applied to the skin of a subject.

In an exemplary embodiment, the immunomodulation may refer to increasing the number of M2 type macrophages and decreasing the number of M1 type macrophages.

In the present disclosure, the "active ingredient" refers to a component which exhibits a desired activity either alone or as used together with a carrier, etc., which is inactive per se.

In an exemplary embodiment, the lactic acid bacteria may be a strain in the genus *Lactobacillus*.

In an exemplary embodiment, the strain in the genus *Lactobacillus* may be preferred to be *Lactobacillus plantarum* in terms of immunomodulatory effect and yield increase of extracellular vesicles including exosomes. The *Lactobacillus plantarum* has an effect of providing superior immunomodulatory effect and superior exosome yield efficiency.

In an exemplary embodiment, the *Lactobacillus plantarum* may be *Lactobacillus plantarum* APsulloc 331261 having an accession number of KCCM11179P. The *Lactobacillus plantarum* APsulloc 331261 was deposited under the Budapest Treaty on the International Recognition of the Deposit of Microorganisms for the Purposes of Patent Procedure at Korean Culture Center of Microorganisms at 361-221, Yurim B/D, Hongje-1-dong, Seodaemun-gu, Seoul, Republic of Korea, on Mar. 28, 2011 and was given Accession No.: KCCM11179P.

In the present disclosure, the "extracellular vesicle" refers to a vesicle secreted from a cell and released into the extracellular space, and means a membrane structure vesicle of which the inside and the outside are distinguished by a lipid bilayer. Since the extracellular vesicle has plasma membrane lipids, plasma membrane proteins, nucleic acids, cytoplasmic components, etc., it allows to identify the properties and state of cells indirectly. In addition, it can bind to other cells or tissues to deliver membrane components, mRNAs, miRNAs, proteins (growth hormone, cytokine, etc.), and transfer these substances to the recipient cells to act as extracellular transporters mediating cell-to-cell communication.

In an exemplary embodiment, the extracellular vesicle may be isolated from the culture of lactic acid bacteria.

In an exemplary embodiment, the extracellular vesicle may be one that precipitates in ultracentrifugation of lactic acid bacteria culture at 100,000×g or higher, specifically at 100,000-200,000×g, 100,000-150,000×g or 150,000-200,000×g.

In an exemplary embodiment, the extracellular vesicle may have a diameter of 20-500 nm. In another aspect, the extracellular vesicle may have a diameter of 20 nm or larger, 30 nm or larger, 40 nm or larger, 50 nm or larger, 60 nm or larger, 70 nm or larger, 80 nm or larger, 90 nm or larger or 100 nm or larger, and 500 nm or smaller, 450 nm or smaller, 400 nm or smaller, 350 nm or smaller, 300 nm or smaller, 250 nm or smaller, 200 nm or smaller, 150 nm or smaller or 100 nm or smaller.

In an exemplary embodiment, the extracellular vesicle may have a diameter of 20-200 nm.

In an exemplary embodiment, the diameter may mean an average diameter.

In an exemplary embodiment, the extracellular vesicle may be an exosome.

In an exemplary embodiment, the extracellular vesicle may be one in which the membrane component is modified chemically or physically, for example, so as to perform a desired function effectively in a target cell. For example, the membrane component of the extracellular vesicle may be modified by a chemical method using a thiol group (—SH) or an amine group (—$NH_2$), or may be modified chemically by a chemical bonding of a target inducing substance, a cell membrane fusion substance or polyethylene glycol to the extracellular vesicle.

In an exemplary embodiment, the extracellular vesicle may be isolated by one or more method selected from a group consisting of centrifugation, ultracentrifugation, differential centrifugation, equilibrium density centrifugation, density gradient, filtration, dialysis and free-flow electrophoresis. However, the method of isolating the extracellular vesicle is not limited thereto.

Density gradient is the most frequently used method when separating substances with different densities. As a specific example, the method may be performed using a density gradient separation material such as ficoll, glycerol, sucrose, cesium chloride, iodixanol, etc., but are not limited thereto. In an aspect, the density gradient may be used together with ultracentrifugation, etc. In another aspect, gel filtration or ultrafiltration may be used to select the extracellular vesicle. In another aspect, dialysis may be used instead of filtration in order to remove small-sized molecules. In another aspect, free-flow electrophoresis may be used.

In an exemplary embodiment, the extracellular vesicle derived from lactic acid bacteria exhibiting effective activity may be prepared by a method comprising: (1) a step of obtaining a supernatant by centrifuging a culture of lactic acid bacteria; (2) a step of filtering the obtained supernatant; and (3) a step of obtaining a precipitate by ultracentrifuging the obtained filtrate.

In an exemplary embodiment, the centrifugation in the step (1) may be performed at 1,000-20,000×g, 1,500-20,000×g, 1,500-15,000×g or 1,500-10,000×g for 30-60 minutes. At this time, the centrifugation may be performed stepwise by changing the speed or time. For example, the centrifugation may be performed at a low speed of 1,500 to 2,000×g to separate and remove the lactic acid bacteria strain from the culture, and then at a high speed of 10,000 to 20,000×g to further remove the cells or cell-related debris and residues, etc.

In an exemplary embodiment, the filtration in the step (2) may be performed using a filter with a size of 0.3-0.5 μm. The purity of the centrifuged culture may be increased through the filtration.

In an exemplary embodiment, the ultracentrifugation in the step (3) may be performed at 100,000×g or higher, specifically 100,000-200,000×g, 100,000-150,000×g or 150,000-200,000×g, for 1-5 hours.

In an exemplary embodiment, the method may further comprise, after the step (3), (4) a step of suspending the obtained precipitate.

In an exemplary embodiment, the extracellular vesicle derived from lactic acid bacteria or the composition comprising the same may induce differentiation into M2 type macrophages. M2 type macrophages form a new blood vessel to heal wounds and reconstitute tissues. Accordingly, a composition comprising the extracellular vesicle derived from lactic acid bacteria according to the present disclosure as an active ingredient may have skin regeneration effect.

In an exemplary embodiment, the extracellular vesicle derived from lactic acid bacteria or the composition comprising the same may increase the number of M2 type macrophages in a subject.

In an exemplary embodiment, the extracellular vesicle derived from lactic acid bacteria or the composition comprising the same may decrease the number of M1 type macrophages in a subject.

In an exemplary embodiment, the extracellular vesicle derived from lactic acid bacteria or the composition comprising the same may increase the expression of one or more selected from a group consisting of CCL19, CCL20 and VEGFA, which are M2 type macrophage differentiation markers.

In an exemplary embodiment, the extracellular vesicle derived from lactic acid bacteria or the composition comprising the same may decrease the expression of one or more selected from a group consisting of CCR2, SOCS3 and HLA-DRα, which are M1 type macrophage differentiation markers.

In an exemplary embodiment, the composition may be a freeze-dried formulation. The composition may be a freeze-dried formulation packaged in a sealed packaging material or container so as to be used immediately (ready-to-use).

In another aspect, the present disclosure provides an immunomodulatory kit comprising: a composition in the form of a freeze-dried formulation, which comprises an extracellular vesicle derived from lactic acid bacteria as an active ingredient; and sterile water or purified water. The kit may be packaged in a sealed packaging material or container so as to be used immediately (ready-to-use).

In an exemplary embodiment, the composition may be a cosmetic composition.

The cosmetic composition may further contain functional additives and ingredients contained in general cosmetic compositions, in addition to the active ingredient. The functional additive may include an ingredient selected from a group consisting of a water-soluble vitamin, an oil-soluble vitamin, a polypeptide, a polysaccharide, a sphingolipid and a seaweed extract. In addition, an oil or fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a fragrance, a blood circulation promoter, a cooling agent, an antiperspirant, purified water, etc. may be used as a blending ingredient.

The formulation of the cosmetic composition is not specially limited and may be selected adequately depending on purposes. For example, the cosmetic composition may be prepared into one or more formulation selected from a group consisting of a powder, a skin lotion, a skin softener, a skin toner, an astringent, lotion, a milk lotion, a moisturizing lotion, a nourishing lotion, a massage cream, a nourishing cream, a moisturizing cream, a hand cream, a foundation, an essence, a nourishing essence, a pack, a shampoo, a soap, a cleansing foam, a cleansing lotion, a cleansing cream, a body lotion and a body cleanser, although not being limited thereto.

When the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

When the formulation of the present disclosure is a powder or a spray, lactose, talc, silica, aluminum hydroxide, calcium silicate or polyamide powder may be used as a carrier ingredient. In particular, when the formulation is a spray, it may further contain a propellant such as chlorofluorohydrocarbon, propane/butane or dimethyl ether.

When the formulation of the present disclosure is a solution or an emulsion, a solvent, a solubilizer or an emulsifier such as water, ethanol, isopropanol, ethyl carbonate, ethyl acetate, benzyl alcohol, benzyl benzoate, propylene glycol, 1,3-butylene glycol, an aliphatic glycerol ester, polyethylene glycol or a fatty acid ester of sorbitan may be used as a carrier ingredient.

When the formulation of the present disclosure is a suspension, a liquid diluent such as water, ethanol or propylene glycol, a suspending agent such as ethoxylated isostearyl alcohol, polyoxyethylene sorbitol ester, polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, an aliphatic alcohol sulfate, an aliphatic alcohol ether sulfate, sulfosuccinic acid monoester, isethionate, an imidazolinium derivative, methyl taurate, sarcosinate, a fatty acid amide ether sulfate, an alkylamido betaine, aliphatic alcohol, a fatty acid glyceride, a fatty acid diethanolamide, a vegetable oil, a lanolin derivative, an ethoxylated glycerol fatty acid ester, etc. may be used as a carrier ingredient.

When the formulation of the present disclosure is a soap, an alkali metal salt of a fatty acid, a fatty acid hemiester, a fatty acid or protein hydrolysate, isethionate, a lanolin derivative, an aliphatic alcohol, a vegetable oil, glycerol, a sugar, etc. may be used as a carrier ingredient.

In an exemplary embodiment, the composition may be a pharmaceutical composition.

The pharmaceutical composition may further contain, in addition to the active ingredient, a pharmaceutical adjuvant such as an antiseptic, a stabilizer, a wetting agent, an emulsification accelerator, a salt and/or buffer for control of osmotic pressure, etc. and other therapeutically useful substances, and may be prepared into various formulations for oral administration or parenteral administration.

The formulation for oral administration may be, for example, a tablet, a pill, a hard or soft capsule, a liquid, a suspension, an emulsion, a syrup, a powder, a fine granule, a granule, a pellet, etc., and these formulations may contain, in addition to the active ingredient, a surfactant, a diluent (e.g., lactose, dextrose, sucrose, mannitol, sorbitol, cellulose or glycine), a lubricant (e.g., silica, talc, stearic acid and its magnesium or calcium salt, or polyethylene glycol). A tablet may further contain a binder such as magnesium aluminum silicate, starch paste, gelatin, tragacanth, methylcellulose, sodium carboxymethylcellulose and polyvinylpyrrolidone, and may optionally contain pharmaceutical additives such as a disintegrant such as starch, agar, alginic acid or its sodium salt, an absorbent, a colorant, a flavor, a sweetener, etc. The tablet may be prepared by common mixing, granulation or coating methods.

The formulation for parenteral administration may be a formulation for transdermal administration, and may be, for example, an injection, a medicinal drop, an ointment, a lotion, a gel, a cream, a spray, a suspension, an emulsion, a suppository, a patch, etc., although not being limited thereto.

Determination of the administration dosage of the active ingredient is within the level of those of ordinary skill. The daily administration dosage varies depending on various factors such as the progress of a disease, the duration of the disease, the age and health condition of a subject, the presence of complications, etc. For an adult, the composition may be administered at a dosage of 1 µg/kg to 200 mg/kg or 50 µg/kg to 50 mg/kg, once to three times a day. However, the administration dosage does not limit the scope of the present disclosure by any means.

The pharmaceutical composition may be a formulation for external application to skin. The formulation for external application to skin refers to any formulation that can be applied externally to the skin, and may include various medical formulations.

In an exemplary embodiment, the composition may be a food composition.

The food composition may be a liquid or solid formulation. For example, it may be in the form of various foods, drinks, gum, tea, vitamin complexes, dietary supplements, powder, granules, tablets, capsules or beverages. The food composition of each formulation may contain commonly used ingredients that can be selected by those skilled in the art without difficulty depending on the formulation type or purpose of use, in addition to the active ingredient.

The liquid ingredients that may be contained in addition to the active ingredient are not particularly limited, and various flavors, natural carbohydrates, etc. may be contained as additional ingredients as in common drinks. Examples of the natural carbohydrate include common sugars such as a monosaccharide such as glucose, fructose, etc., a disaccharide such as maltose, sucrose, etc. and a polysaccharide such as dextrin, cyclodextrin, etc. and sugar alcohols such as xylitol, sorbitol, erythritol, etc. As the flavor, a natural flavor (e.g., thaumatin, stevia extract, rebaudioside A, glycyrrhizin, etc.) or a synthetic flavor (e.g., saccharin, aspartame etc.) may be advantageously used. The proportion of the natural carbohydrate may be generally about 1-20 g, specifically about 5-12 g, based on 100 mL of the composition of the present disclosure.

The food composition may contain various nutrients, vitamins, minerals (electrolytes), flavors such as synthetic flavors, natural flavors, etc., colorants, extenders (cheese, chocolate, etc.), pectic acid and its salts, alginic acid and its salts, organic acid, protective colloidal thickeners, pH control agents, stabilizers, antiseptics, glycerin, alcohols, carbonating agents used in carbonated beverages, etc. In addition, it may contain pulp for preparing natural fruit juice or vegetable beverages. These ingredients may be used independently or in combination. The proportion of the additives may vary, but is generally chosen in a range from 0.001 to about 20 parts by weights based on 100 parts by weight of the composition of the present disclosure.

MODE FOR INVENTION

Hereinafter, the present disclosure will be described in detail through examples. However, it will be obvious to those of ordinary skill in the art that the following examples are for illustrative purposes only and the scope of the present disclosure is not limited by the examples.

Example 1. Isolation of Extracellular Vesicles Derived from Lactic Acid Bacteria Extracellular vesicles including exosomes were isolated from a strain in the genus *Lactobacillus*. More specifically, extracellular vesicles derived from lactic acid bacteria were prepared using a *Lactobacillus plantarum* APsulloc 331261 (Accession No.: KCCM11179P) strain.

(Step 1) The culture solution of the cultured strain in the genus *Lactobacillus* was centrifuged at 4° C. and 1,800×g for 20 minutes to separate and remove the strain in the genus *Lactobacillus* from the culture solution. That is to say, the cells were separated from the supernatant through low-speed centrifugation.

(Step 2) The culture solution centrifuged in the step 1 was centrifuged at 4° C. and 10,000×g for 20 minutes by using a high-speed centrifuge to further remove cells or cell-related debris and residues, etc.

(Step 3) The culture solution centrifuged in the step 2 was filtered through a 0.45-µm bottle top filter to increase the purity of the culture solution.

(Step 4) The culture solution filtered in the step 3 was ultracentrifuged at 4° C. and 150,000×g for 3 hours to separate extracellular vesicles including exosomes.

(Step 5) After the ultracentrifugation in the step 4, the supernatant was removed and the remaining pellet of extracellular vesicles including exosomes was resuspended in a HEPES buffer.

Figure 1:
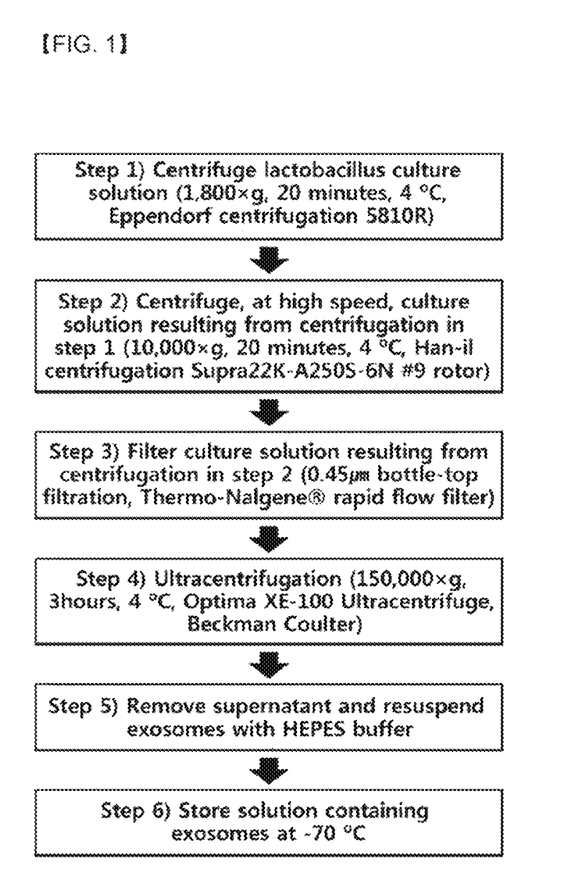
FIG. 1 shows a process of isolating extracellular vesicles from lactic acid bacteria according to an exemplary embodiment of the present disclosure.

(Step 6) The extracellular vesicles (EVs) including exosomes resuspended in the buffer in the step 5 were stored at −70° C. and used in the following test (see FIG. 1).

Comparative Example 1. Preparation of Lactic Acid Bacteria Cells

Cells of lactic acid bacteria were prepared using the *Lactobacillus plantarum* APsulloc 331261 (Accession No.

KCCM11179P) strain used in Example 1 and used in the following test. In other words, the lactic acid bacterial cells of the present Comparative Example mean the intact whole cells that have not undergone a process of separating the extracellular vesicles.

Test Example 1. Identification of Extracellular Vesicles Derived from Lactic Acid Bacteria (LEVs)

Figure 2A:
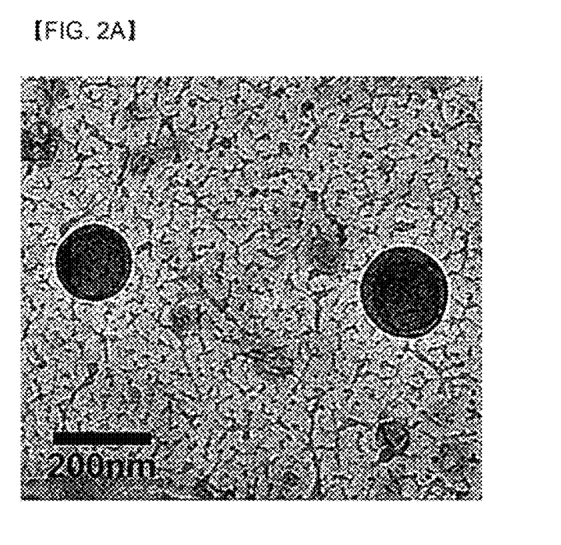
FIG. 2A shows a transmission electron microscopic image of extracellular vesicles derived from lactic acid bacteria according to one test example of the present disclosure.
Figure 2B:
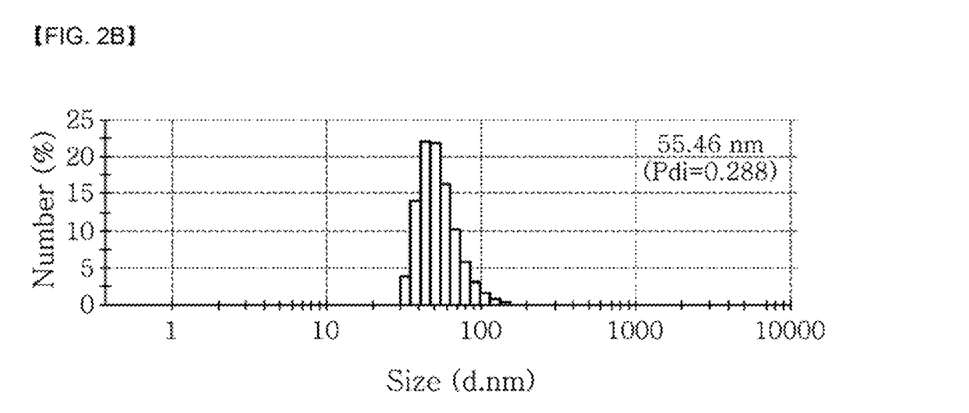
FIG. 2B shows a result of measuring the size of extracellular vesicles derived from lactic acid bacteria according to one test example of the present disclosure.

The shape and size of the extracellular vesicles derived from lactic acid bacteria isolated in Example 1 were analyzed by transmission electron microscopy and dynamic light scattering (DLS). In general, they had spherical shapes and had a diameter of about 20-200 nm (see FIGS. 2A and 2B). A PDI (polydispersity index) value stands a heterogeneity index, and the isolated extracellular vesicles were found to be dispersed relatively stably and homogeneously. The isolated extracellular vesicles had an average diameter of about 50-60 nm, more specifically 55.46 nm.

Test Example 2. Effect on Cell Proliferation and Cytotoxicity

After treating human fibroblasts (Hs68) with the extracellular vesicles derived from lactic acid bacteria isolated in Example 1 (0.1-10 µg/mL), the effect on cell proliferation and cytotoxicity was investigated.

Specifically, human fibroblasts Hs68 were incubated in a $CO_2$ incubator and treated with the extracellular vesicles derived from lactic acid bacteria isolated in Example 1 at 0.1 µg/mL, 1 µg/mL or 10 µg/mL. Then, the cells were incubated for 48 hours under a serum-free condition. A positive control group was treated with 5 ng/mL TGF-β. Then, after replacing the medium with a medium containing 5% CCK-8 and incubating further for 2 hours, cell proliferation and cytotoxicity were compared with the control group by measuring absorbance at 450 nm.

Figure 3:
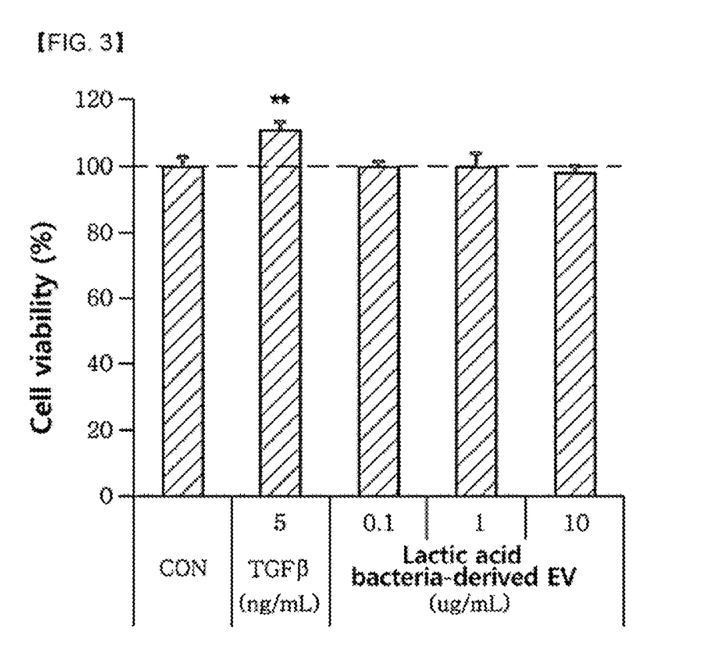
FIG. 3 shows a result of treating dermal fibroblasts with extracellular vesicles derived from lactic acid bacteria and measuring the effect on cell proliferation and cytotoxicity according to one test example of the present disclosure (**; $p<0.01$).

As seen from FIG. 3, the extracellular vesicles derived from lactic acid bacteria did not affect the cell proliferation and were safe in the absence of cytotoxicity.

Test Example 3. Effect on Undifferentiated Macrophages 1

Undifferentiated human macrophages (monocytic THP1) were treated with the extracellular vesicles derived from lactic acid bacteria isolated in Example 1 and differentiation was induced with PMA (phorbol 12-myristate 13-acetate). Then, the expression of macrophage differentiation markers was investigated.

Specifically, THP1 cells were treated for 48 hours with 10 µg/mL EV and 20 nM PMA at the same time or individually. After recovering the cells, RNA was purified and cDNA was synthesized. The cDNA obtained from 100 ng of RNA was subjected to qRT-PCR analysis, and the result was normalized to the result for the GAPDH gene.

Figure 4:
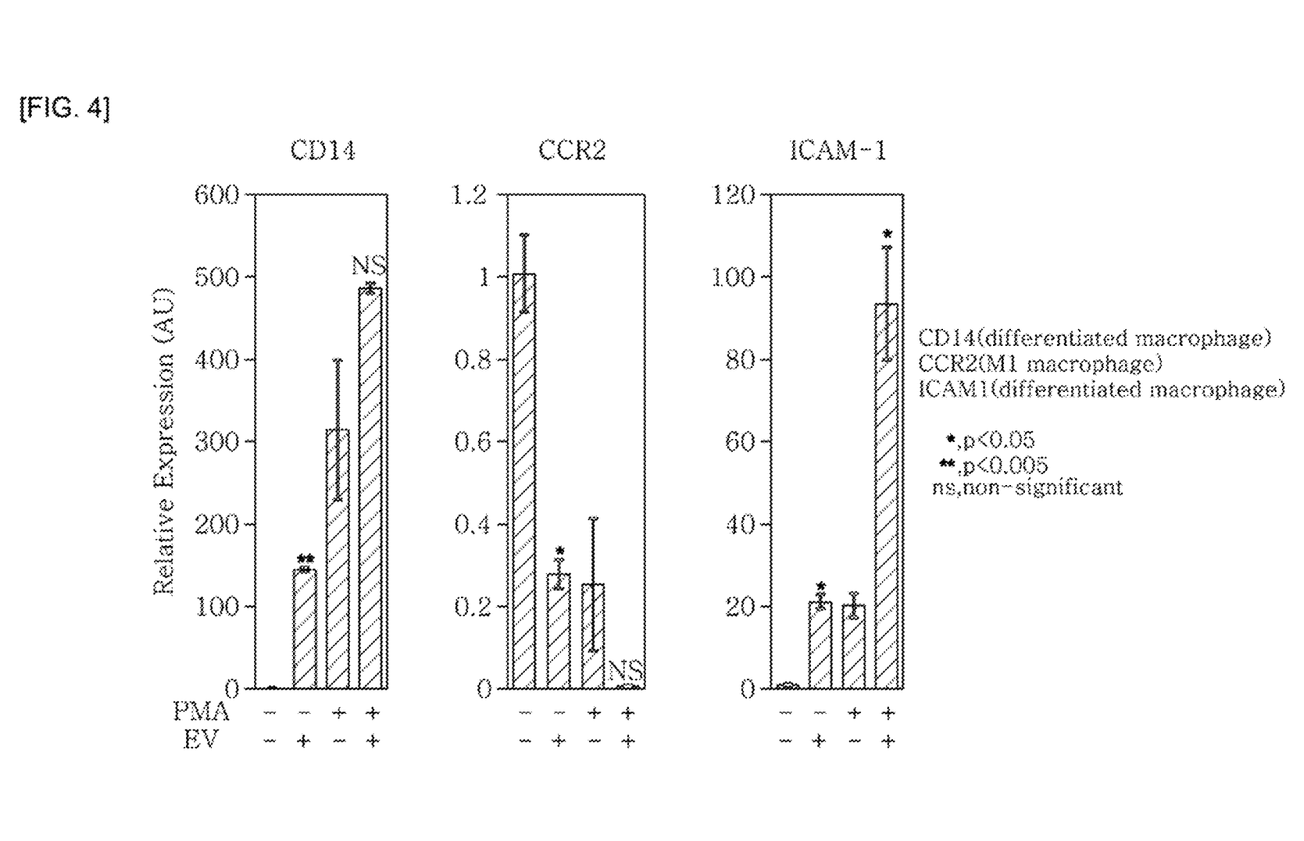
FIG. 4 shows a result of investigating the effect of extracellular vesicles derived from lactic acid bacteria on undifferentiated macrophages according to one test example of the present disclosure.

As seen from FIG. 4, the isolated extracellular vesicles derived from lactic acid bacteria induced the expression of macrophage differentiation markers CD14 and ICAM-1 comparably to the strong differentiation inducer PMA, even in the absence of PMA. They decreased the expression of the M1 marker CCR2, and showed synergistic effect when treated together with PMA. That is to say, the isolated extracellular vesicles derived from lactic acid bacteria effectively induced the differentiation of macrophages comparably to PMA.

Test Example 4. Effect on Undifferentiated Macrophages 2

The differentiation pattern of macrophages was investigated by treating undifferentiated human macrophages (monocytic THP1) with the extracellular vesicles derived from lactic acid bacteria isolated in Example 1.

Specifically, undifferentiated human macrophages (monocytic THP1) were treated first with 20 nM PMA for 48 hours. Then, after treating with 10 µg/mL EVs or cytokines for inducing M1 and M2 differentiation further for 48 hours, the expression of representative genes for M1 and M2 was compared. For induction of M1 differentiation, the cells were treated with 20 ng/mL IFN-gamma and 10 µg/mL LPS. For induction of M2 differentiation, 20 ng/mL interleukin 4 (R&D Systems, #204-IL) and 20 ng/mL interleukin 13 (R&D Systems, #213-ILB) were used. Then, after recovering the cells, RNA was purified and cDNA was synthesized. The cDNA obtained from 100 ng of RNA was subjected to qRT-PCR analysis, and the result was normalized to the result for the GAPDH gene.

Figure 5:
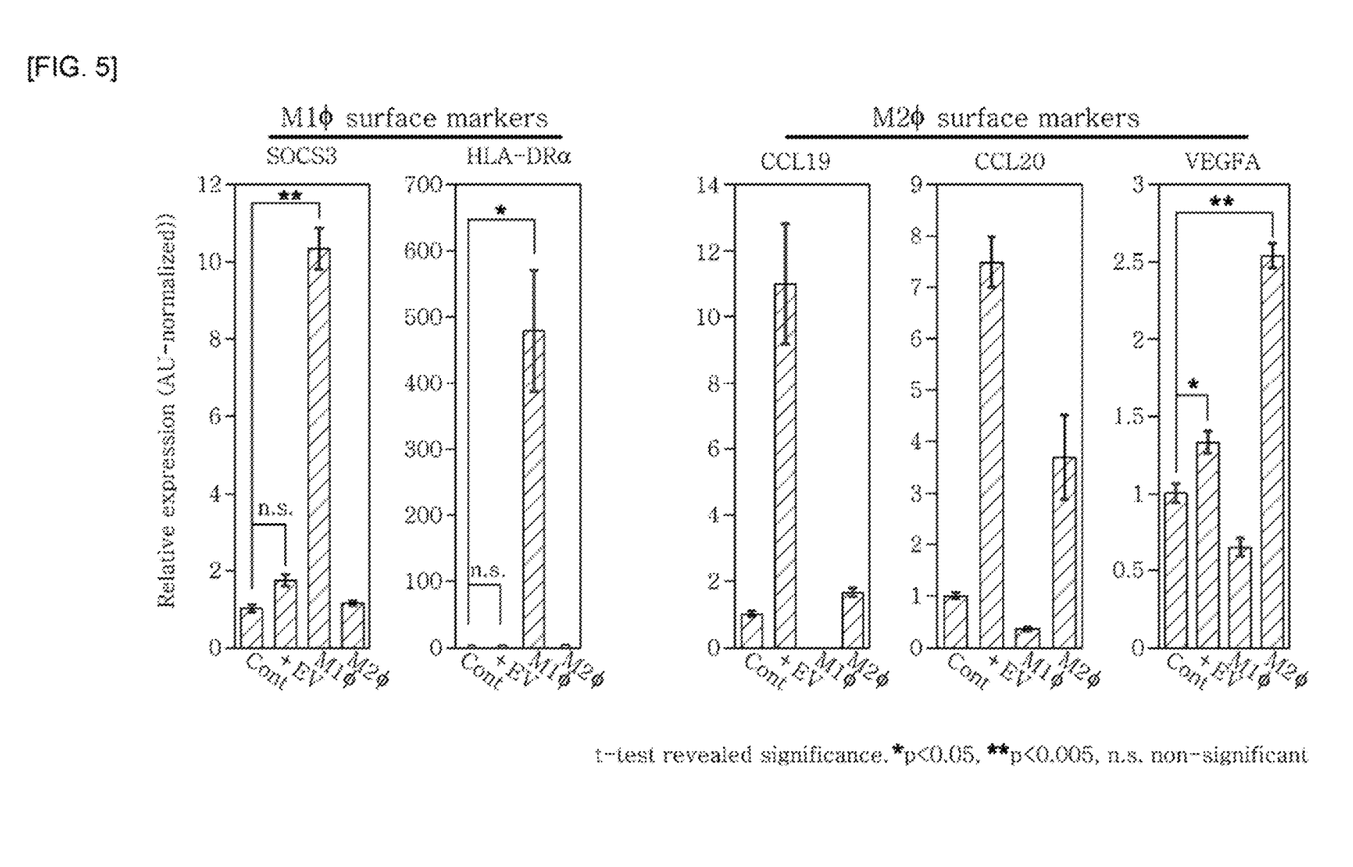
FIG. 5 shows a result of investigating the effect of extracellular vesicles derived from lactic acid bacteria on undifferentiated macrophages according to one test example of the present disclosure.

As seen from FIG. 5, the isolated extracellular vesicles derived from lactic acid bacteria induced the expression of the M2 type markers CCL19, CCL20 and VEGFA, which have the ability of recovering and reconstituting damaged tissues, and decreased the expression of the M1 markers SOCS3 and HLA-DRα when treated to the undifferentiated human macrophages. Accordingly, it can be seen that the isolated extracellular vesicles derived from lactic acid bacteria have the effect of inducing M2 differentiation.

Test Example 5. Effect on M1 Type Macrophages

After treating macrophages differentiated into M1 type using PMA (phorbol 12-myristate 13-acetate) with the extracellular vesicles derived from lactic acid bacteria isolated in Example 1, the expression level of M1 type macrophage markers was investigated.

Specifically, after treating undifferentiated human macrophage with 20 nM PMA for 48 hours, experiment was performed in the presence (left graph in FIG. 6) or absence (right graph in FIG. 6) of PMA. The cells were treated first selectively with 10 µg/mL EVs or M1-inducing cytokines (20 ng/mL IFN-gamma, 10 µg/mL LPS) for 48 hours and then subsequently with M1 differentiation-inducing cytokines or EVs respectively for 48 hours. After recovering the cells, RNA was purified and cDNA was synthesized. The cDNA obtained from 100 ng of RNA was subjected to qRT-PCR analysis, and the result was normalized to the result for the GAPDH gene. The effect of the EVs, the inhibitory effect on M1 differentiation induction and the effect on dedifferentiation of the M1-differentiated cells were analyzed. The right graph in FIG. 6 shows the result of removing the initially treated PMA and performing the same experiment.

Figure 6:
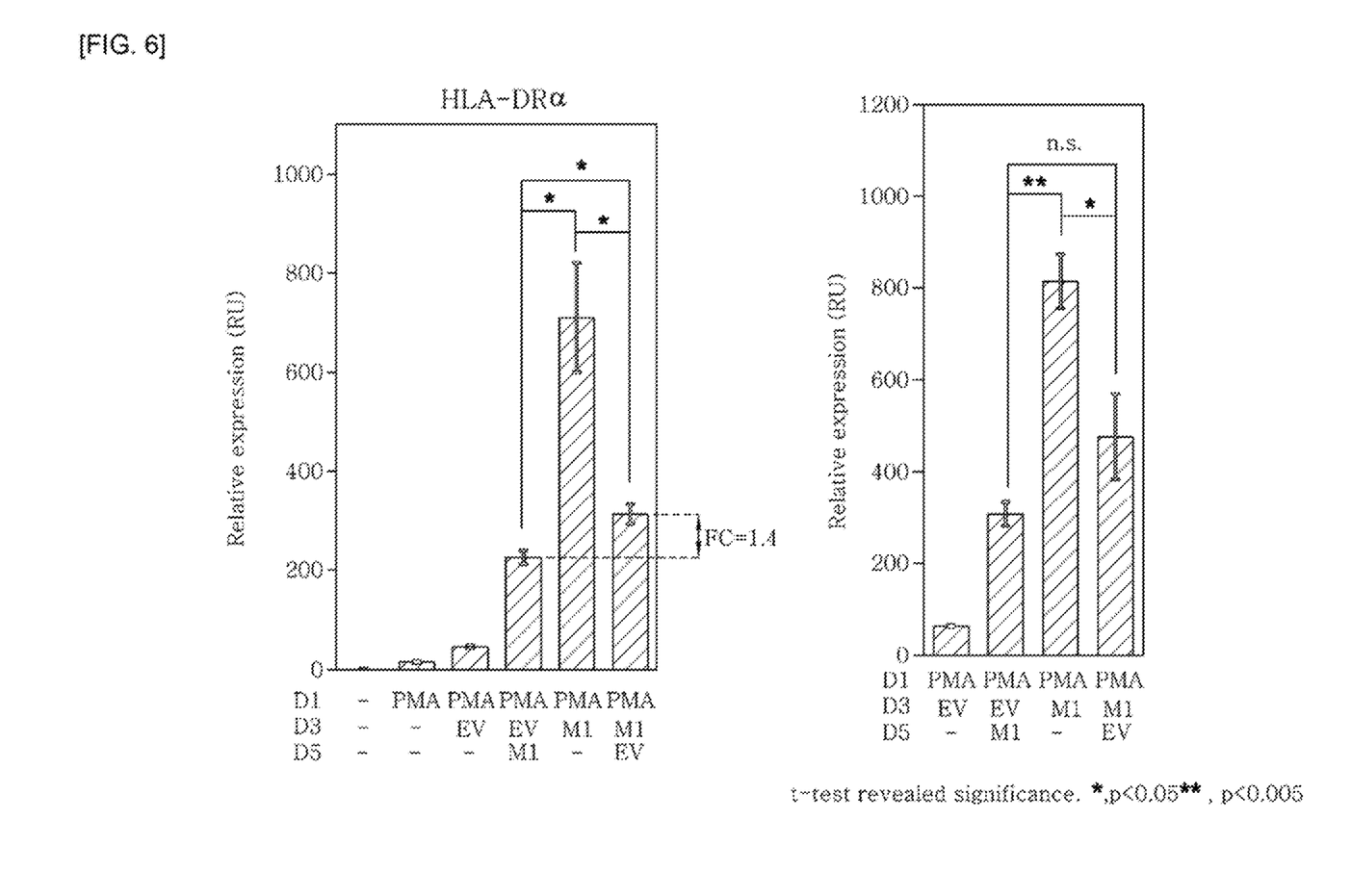
FIG. 6 shows a result of investigating the effect of extracellular vesicles derived from lactic acid bacteria on the expression level of M1 type macrophage markers according to one test example of the present disclosure.

As seen from FIG. 6, the expression of HLA-DR alpha, which is a M1 macrophage marker, was decreased by the pre/post-treatment of EVs under both conditions. Accordingly, it can be seen that the extracellular vesicles derived from lactic acid bacteria can differentiate monocytes into macrophages, induces differentiation into M2 type, which contributes to tissue regeneration, and can dedifferentiate the differentiated M1 type.

Test Example 6. Comparison of Effect on Immune Cells

The effect of the extracellular vesicles derived from lactic acid bacteria isolated in Example 1 and the lactic acid bacteria cells prepared in Comparative Example 1 on immune cells was compared.

Specifically, THP1 cells were treated with the extracellular vesicles derived from lactic acid bacteria or lactic acid bacteria cells of the same quantity in order to investigate their effect on cell activity. After recovering the cells, RNA was purified and cDNA was synthesized. The cDNA obtained from 100 ng of RNA was subjected to qRT-PCR analysis, and the result was normalized to the result for the GAPDH gene.

Figure 7:
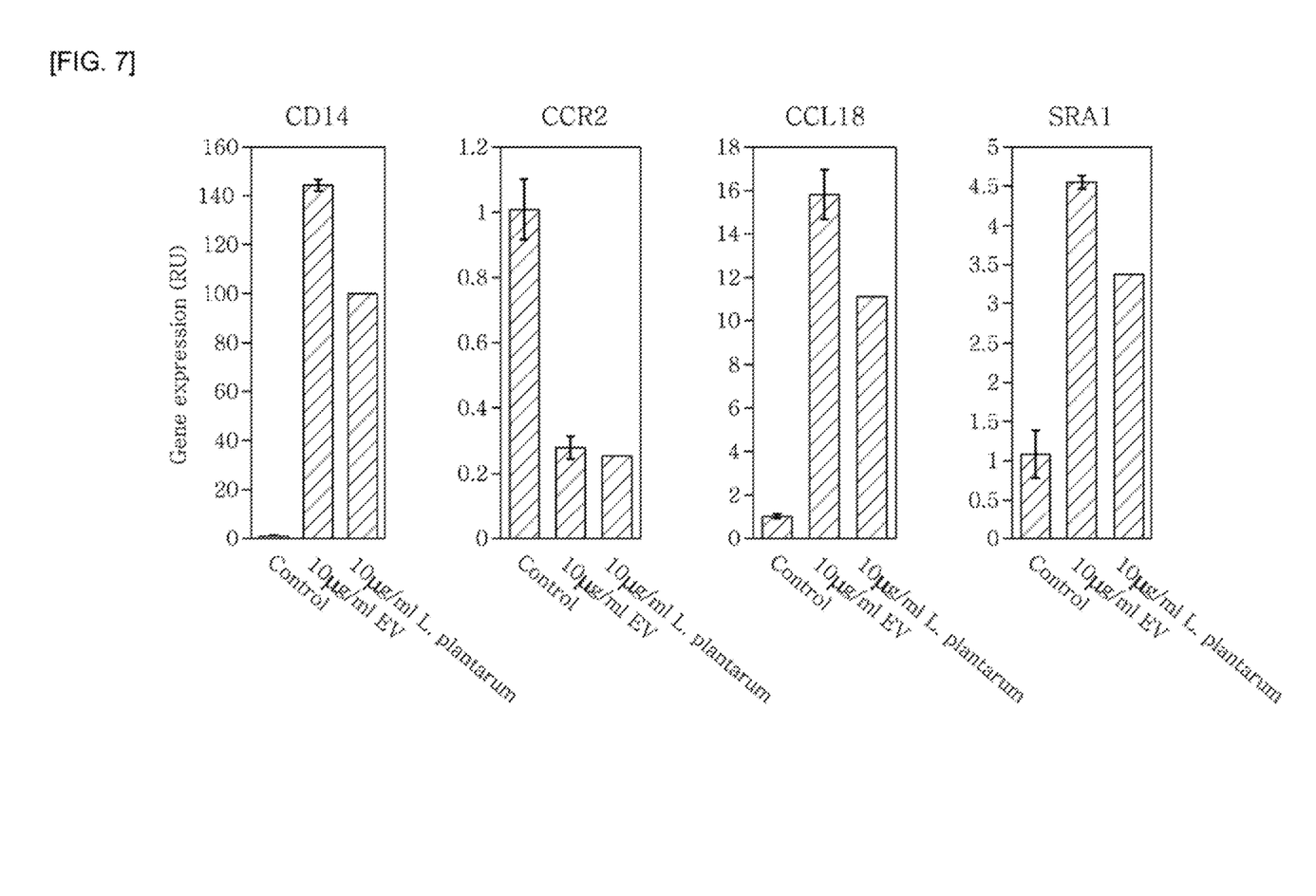
FIG. 7 shows a result of comparing the effect of extracellular vesicles derived from lactic acid bacteria and cells of lactic acid bacteria on immune cells according to one test example of the present disclosure.

As seen from FIG. 7, the extracellular vesicles derived from lactic acid bacteria showed comparable or better ability of inducing or inhibiting the expression of differentiation-related genes of the immune cells as compared to the lactic acid bacteria cells of the same quantity.

Test Example 7. Comparison of Cytotoxicity

The effect of the extracellular vesicles derived from lactic acid bacteria isolated in Example 1 and the lactic acid bacteria cells prepared in Comparative Example 1 on cytotoxicity was compared.

Specifically, human fibroblasts Hs68 were incubated in a 5% $CO_2$ incubator at 37° C. and then treated with the extracellular vesicles derived from lactic acid bacteria isolated in Example 1 or the lactic acid bacteria cells prepared in Comparative Example 1 at 1-20 μg/mL for 72 hours. Then, the supernatant was recovered and the LDH activity was measured. The cytotoxicity was measured using the Pierce™ LDH cytotoxicity assay kit according to the manufacturer's instructions.

Figure 8:
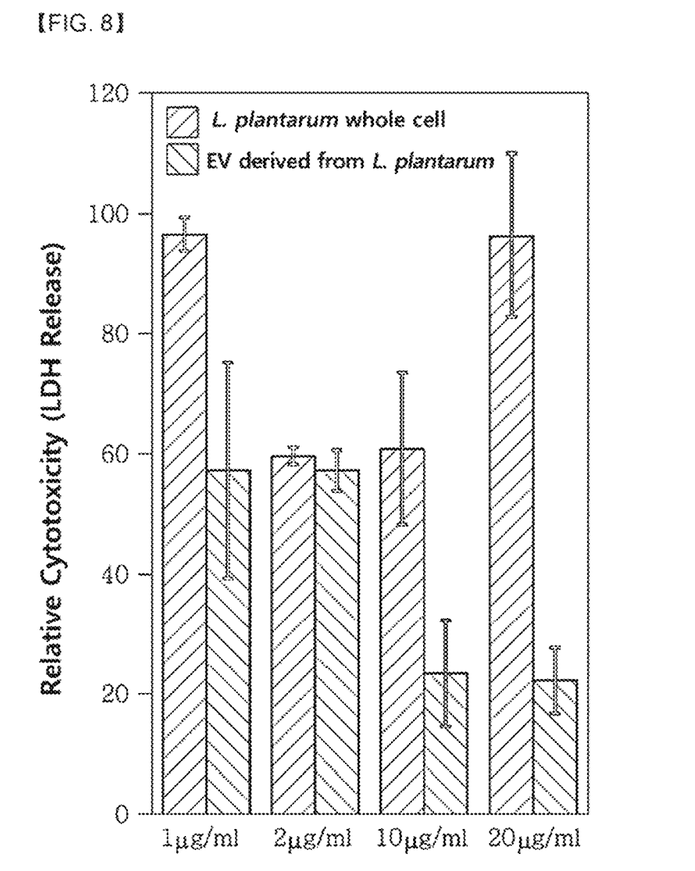
FIG. 8 shows a result of comparing the effect of extracellular vesicles derived from lactic acid bacteria and cells of lactic acid bacteria on cytotoxicity according to one test example of the present disclosure.

As seen from FIG. 8, the extracellular vesicles derived from lactic acid bacteria showed superior effect of protecting cells from cytotoxicity by remarkably reducing cytotoxicity as compared to the lactic acid bacteria cells, when treated above certain concentrations.

Hereinafter, the present disclosure will be described in detail through formulation examples. However, the following examples are for illustrative purposes only and the scope of the present disclosure is not limited by the examples.

Formulation Example 1. Ointment

An ointment was prepared according to a common method with the composition described in Table 1.

TABLE 1

| Ingredients | Contents (wt %) |
|---|---|
| Extracellular vesicles derived from lactic acid bacteria of Example 1 | 2.00 |
| Glycerin | 8.00 |
| Butylene glycol | 4.00 |
| Liquid paraffin | 15.00 |
| β-Glucan | 7.00 |
| Carbomer | 0.10 |
| Caprylic/capric triglyceride | 3.00 |
| Squalane | 1.00 |
| Cetearyl glucoside | 1.50 |
| Sorbitan stearate | 0.40 |
| Cetearyl alcohol | 1.00 |
| Beeswax | 4.00 |
| Purified water | balance |
| Total | 100.00 |

Formulation Example 2. Beauty Care Solution

A beauty care solution was prepared according to a common method with the composition described in Table 2.

TABLE 2

| Ingredients | Contents (wt %) |
|---|---|
| Extracellular vesicles derived from lactic acid bacteria of Example 1 | 2.00 |
| Hydroxyethyl cellulose (2% aqueous solution) | 12.00 |
| Xanthan gum (2% aqueous solution) | 2.00 |
| 1,3-Butylene glycol | 6.00 |
| Concentrated glycerin | 4.00 |
| Sodium hyaluronate (1% aqueous solution) | 5.00 |
| Purified water | balance |
| Total | 100.00 |

Formulation Example 3. Lotion

A lotion was prepared according to a common method with the composition described in Table 3.

TABLE 3

| Ingredients | Contents (wt %) |
|---|---|
| Extracellular vesicles derived from lactic acid bacteria of Example 1 | 2.00 |
| Magnesium L-ascorbyl-2-phosphate | 1.00 |
| Water-soluble collagen (1% aqueous solution) | 1.00 |
| Sodium citrate | 0.10 |
| Citric acid | 0.05 |
| Licorice extract | 0.20 |
| 1,3-Butylene glycol | 3.00 |
| Purified water | balance |
| Total | 100.00 |

Formulation Example 4. Cream

A cream was prepared according to a common method with the composition described in Table 4.

TABLE 4

| Ingredients | Contents (wt %) |
|---|---|
| Extracellular vesicles derived from lactic acid bacteria of Example 1 | 2.00 |
| Polyethylene glycol monostearate | 2.00 |
| Self-emulsifying glyceryl monostearate | 5.00 |
| Cetyl alcohol | 4.00 |
| Squalane | 6.00 |
| Glyceryl tri-2-ethylhexanoate | 6.00 |
| Sphingoglycolipid | 1.00 |
| 1,3-Butylene glycol | 7.00 |
| Purified water | balance |
| Total | 100.00 |

Formulation Example 5. Pack

A pack was prepared according to a common method with the composition described in Table 5

TABLE 5

| Ingredients | Contents (wt %) |
|---|---|
| Extracellular vesicles derived from lactic acid bacteria of Example 1 | 2.00 |
| Polyvinyl alcohol | 13.00 |
| Magnesium L-ascorbyl-2-phosphate | 1.00 |
| Lauroylhydroxyproline | 1.00 |

TABLE 5-continued

| Ingredients | Contents (wt %) |
|---|---|
| water-soluble collagen(1% aqueous solution) | 2.00 |
| 1,3-Butylene glycol | 3.00 |
| ethanol | 5.00 |
| purified water | balance |
| Total | 100.00 |

So far, specific portions of the present disclosure have been described in detail. It will be obvious to one of ordinary skill in the art that this specific description is only a preferred embodiment and that the scope of the present disclosure is not limited thereby. Accordingly, the actual scope of the present disclosure will be defined by the appended claims and their equivalents.

The invention claimed is:

1. An immunomodulatory method comprising administering an extracellular vesicle derived from lactic acid bacteria in an amount effective for immunomodulation to a subject in need thereof, wherein the immunomodulation induces differentiation into M2 type macrophages, and the lactic acid bacteria are *Lactobacillus plantarum* APsulloc 331261 with accession number of KCCM11179P.

2. The immunomodulatory method according to claim 1, wherein the extracellular vesicle is an exosome.

3. The immunomodulatory method according to claim 1, wherein the extracellular vesicle has a diameter of 20-200 nm.

4. The immunomodulatory method according to claim 1, wherein the extracellular vesicle increases expression of one or more selected from the group consisting of CCL19, CCL20, and VEGFA (vascular endothelial growth factor A), which are M2 type macrophage differentiation markers.

5. The immunomodulatory method according to claim 1, wherein the extracellular vesicle decreases expression of one or more M1 type macrophage differentiation markers selected from the group consisting of CCR2 (C-C motif chemokine receptor 2), SOCS3 (suppressor of cytokine signaling 3), and HLA-DRα (human leukocyte antigen—DRα).

6. The immunomodulatory method according to claim 1, wherein the extracellular vesicle is administered in the form of a composition, and the composition is a cosmetic composition.

7. The immunomodulatory method according to claim 1, wherein the extracellular vesicle is administered in the form of a composition, and the composition is a food composition.

* * * * *